United States Patent
Görge et al.

(10) Patent No.: US 6,277,305 B1
(45) Date of Patent: *Aug. 21, 2001

(54) COBALTOUS OXIDE CONTAINING FINELY-DISPERSED METALLIC COBALT, METHODS OF PRODUCING THE SAME AND USE THEREOF

(75) Inventors: Astrid Görge; Juliane Meese-Marktscheffel, both of Goslar; Dirk Naumann, Bad Harzburg; Armin Olbrich, Seesen; Frank Schrumpf, Goslar, all of (DE)

(73) Assignee: H. C. Starck GmbH & Co. KG, Goslar (DE)

( * ) Notice: Subject to any disclaimer, the term of this patent is extended or adjusted under 35 U.S.C. 154(b) by 0 days.

This patent is subject to a terminal disclaimer.

(21) Appl. No.: 08/894,215

(22) PCT Filed: Jan. 29, 1996

(86) PCT No.: PCT/EP96/00336

§ 371 Date: Dec. 17, 1999

§ 102(e) Date: Dec. 17, 1999

(87) PCT Pub. No.: WO96/24556

PCT Pub. Date: Aug. 15, 1996

(30) Foreign Application Priority Data

Feb. 10, 1995 (DE) ............................ 195 04 319

(51) Int. Cl.$^7$ ................. H01B 1/02; H01B 1/08
(52) U.S. Cl. ............. 252/518.1; 252/500; 252/513; 420/435; 423/992; 429/218; 429/209; 205/586; 148/674; 556/138
(58) Field of Search .............. 420/435; 423/592; 429/218, 209; 205/587; 148/674; 556/138; 252/500, 518.1, 513

(56) References Cited

U.S. PATENT DOCUMENTS

| 3,775,352 | 11/1973 | Leonard, Jr. | 260/2.5 B |
| 5,032,475 | 7/1991 | Hasebe et al. | 429/60 |
| 5,053,292 | 10/1991 | Hasebe et al. | 429/101 |
| 5,972,306 | * 10/1999 | Gorge et al. | 423/592 |

FOREIGN PATENT DOCUMENTS

| 2327180 | 5/1973 | (DE) | 257/523 |
| 0 353 837 | 2/1990 | (EP) | H01M/4/52 |
| 0 353 284 | 1/1993 | (EP) | H01M/4/52 |

OTHER PUBLICATIONS

International Preliminary Examination Report for International Application No. PCT/EP96/00336, International Filing Date Jan. 29, 1996, International Patent Classification IPC no. C01G51/04, dated Apr. 30, 1997.
Chem Abstracts 96: 114829 Khokhlacheva: Production and thermal decomposition of formates of some nonferrous metals (from Russian language document) (Apr. 5, 1982).
I. Matsumoto et al., Ni–Fe Battery, Abstract No. 10, 162d ECS Fall Meeting, Detroit, p. 18. (1982).
M. Oshitani, Nickel Positive Electrode for Alkali Cell, 10/209 Patents Abstracts of Japan E–421 (Jul. 22, 1986).
M. Onishi, Nickel Electrode for Alkaline Storage Battery, 15/250 Patents Abstracts of Japan E–1082 (Jun. 26, 1991).
H. Kido, Nickel Electrode, 17/668 Patents Abstracts of Japan E–1473 (Dec. 9, 1993).

* cited by examiner

Primary Examiner—Yogendra N. Gupta
Assistant Examiner—Derrick G Hamlin
(74) Attorney, Agent, or Firm—Joseph C. Gil; Diderico van Eyl

(57) ABSTRACT

The present invention relates to cobalt(II) oxide containing metallic cobalt, to a process for the production thereof and to the use thereof.

10 Claims, No Drawings

COBALTOUS OXIDE CONTAINING FINELY-DISPERSED METALLIC COBALT, METHODS OF PRODUCING THE SAME AND USE THEREOF

The present invention relates to cobalt(II) oxide containing metallic cobalt, the procedure for the production thereof and to the use thereof.

Cobalt(II) oxide is used mixed with metallic cobalt as an additive in the positive composition for rechargeable alkaline Ni batteries based on Ni/Cd or Ni/NiH. For this purpose, NI(OH)2 is processed with the Cobalt(II) oxide/metal mixture and auxiliary substances to yield pastes, which are then incorporated into an electrically conductive electrode carrier. The electrodes produced in this manner are further processed by drying and/or sintering in order to obtain batteries of the most varied types.

In the production of button cells, the electrochemically active electrode constituents are compressed, together with auxiliary substances, principally araphite or nickel powder, into tablets of various sizes. The proportion of the cobalt in the electrode compositions in such cases is between 2 and 10 wt. %.

According to EP-A 353 837, the principal action of the cobalt metal is based on the phenomenon that during the first charge cycles (forming cycles), the cobalt metal is initially oxidised in accordance with its potential to divalent cobalt and may thus dissolve in the alkaline electrolyte. The resultant $Co_{2+}$ ions and -nose possibly already present then diffuse towards the surface of the nickel hydroxide. Here, as battery charging, continues, the ions are oxidised to Co(III) in the form of CoO(OH). This in turn forms a layer on the surface of the nickel hydroxide particles and, in subsequent battery charging and discharging cycles, ensures the electrical conductivity of the electrode material.

$Co^{2+}$ ions may, however, also enter the layer lattice of the nickel hydroxide and there modify the properties of the hydroxide in such a manner that greater charging efficiency of the electrode material is achieved. In addition to the already stated properties, the cobalt used in the electrode composition may act as a safety reserve in the event of excessive discharging. In this case, $Co^{2+}$ ions are again reduced electrochemically and so prevent any evolution of hydrogen. Cobalt compounds with the above-stated properties are also disclosed in patents U.S. Pat. Nos. 5,032,475 and 5,053,292 and in European patent application EP-A 523 284.

Only up to approximately 50% of the cobalt metal powder may be utilised in the electrode for the charging and discharging cycles on electrochemical oxidation, as the predominant proportion of the cobalt is coated with a stable oxide layer. This protective layer in turn prevents the formation of $Co_{2+}$ ions which, as has already been mentioned, are necessary for activation of the electrodes. In order to circumvent this difficulty, soluble cobalt compounds such as cobalt hydroxide or monoxide have hitherto also been incorporated into the electrode composition. This ensured that $Co_{2+}$ ions were already dissolved in the electrolyte prior to electrochemical forming and these ions could already be deposited on the surface of the nickel hydroxide (Matsumo et al.: The 162nd ECS Fall Meeting, Detroit 18, (1982)).

According to the prior art, the Cobalt(II) oxide used for the above-described applications was produced industrially by the thermal decomposition of cobalt carbonate, cobalt hydroxide or higher cobalt oxides. However, in line with the thermodynamic equilibrium, these always contain an excess of oxygen and thus residual amounts of Co(III), However, slight traces of Co(III) in the Cobalt(II) oxide autocatatytically catalyse, the oxidation of divalent cobalt to trivalent cobalt. This latter compound does not, however, form any compounds soluble in the electrolyte so that the conductive layer cannot be formed by means of the mechanism described above. As a consequence, a high degree of electrode utilisation may be achieved only if the content of Co(III) is as low as possible.

One possibility for avoiding the presence of Co(III), and for producing a low cobalt metal content, is to calcine the above-stated starting materials such as cobalt carbonate, cobalt hydroxides and/or cobalt oxides under inert gas in the presence of appropriate quantities of hydrogen. However, this process entails complex process control, i.e. very thorough mixing and constant adjustment of hydrogen apportionment to fluctuations in throughput, which are difficult to avoid on an industrial scale. Only in this case is consistent product quality with uniform distribution of the metallic cobalt ensured.

The object of the present invention is thus to provide a Cobalt(II) oxide containing cobalt metal, which oxide does not exhibit the disadvantages described above.

Corresponding cobalt(II) oxides may be obtained by a process for the production of cobalt(II) oxide containing metallic cobalt, which process is based lipon reacting aqueous cobalt chloride and/or nitrate and/or sulphate solutions with alkali metal and/or alkaline earth metal and/or ammonium carbonate and/or hydrogen carbonate and/or hydroxide and an organic compound containing at least one carboxyl group, wherein a coprecipitate of the general formula

is obtained, wherein the sum is I:!~a+b+c+d:!~1.5 and R denotes two identical or different carboxylic acid residues, the molar ratio of which d/(a+b+c+d) is adjusted in accordance with their reductive capacity, and, once separated from the solution, the coprecipitate is calcined. The present invention provides such a process.

It is generally known that on thermal decomposition cobalt oxalate breaks down into cobalt metal and carbon dioxide.

Tartaric acid also behaves similarly.

The decomposition products of versatic acid residues are, for example, unsaturated hydrocarbons, which may themselves have a reducing action. The reductive capacity of acids with a complicated structure and the derivatives thereof must be determined experimentally. It is important that the only organic acid residues used are those which yield no solid decomposition products on calcination, in order to avoid contamination of the product with carbon.

Thanks to the incorporation of reducing anions into the crystal lattice of the coprecipitate, the component with the reducing action is optimally distributed and it is possible to achieve a much more uniform distribution of the metallic cobalt than is possible with gas phase reduction.

Carboxylic acids may preferably be used in the process according to the invention as the organic compound containing at least one carboxyl group. Suitable carboxylic acids are in particular linear or branched, saturated or unsaturated monocarboxylic acids with a number of C atoms from 1 to 9 and/or linear or branched, saturated or unsaturated polycarboxylic acids with a number of C atoms from 2 to 10 and/or cyclic or heterocyclic, saturated or unsaturated mono- and polycarboxylic acids with a number of C atoms from 4 to 14 and/or linear or branched, saturated or unsaturated mono- and polycarboxylic acids with a number of C atoms from 2 to 7 and/or aromatic hydroxycarboxylic acids with a number of C atoms from 7 to 11 and/or cyclic or aliphatic, saturated or unsaturated ketocarboxylic- acids With a number of C atoms from 2 to 14.

Adipic acid, succinic acid, glutaric acid, glyoxylic acid, maleic acid, malonic acid, lactic acid, oxalic acid, phthalic acids, mucic acid, sorbic acid, racemic taxtaric acid, versatic acid, tartaric acid and/or citric acid may also advantageously be used.

In another advantageous event of the process according to the invention, the carboxylic acids may also be used in partially esterified form, providing that they still have at least one active carboxyl group.

The reaction according to the invention is preferably performed in a temperature range from 20° C. to 100° C., preferably 25° C. to 85° C.

It is assumed that, as reduction begins in the crystal lattice, individual cobalt atoms are initially formed which combine by diffusion processes to yield clusters and finally fine deposits of cobalt. As a consequence, the size of the cobalt particles is influenced not only by the concentration of the metallic cobalt in the product but also by the calcination temperature.

Calcination is preferably performed in an inert gas atmosphere at temperatures of between 200° C. and 1100° C., particularly preferably 600° C. and 1000° C. In this manner, cobalt particles of a size of the order of <100 nm are obtained at moderate temperatures of approximately 600° C., while particles in the μm range are obtained at higher calcination temperatures.

The present invention also provides a Co(II) oxide containing finely divided metallic cobalt obtainable in accordance with the process according to the invention, which oxide has a cobalt content of the order of between 78 and 98%, preferably 79 to 91%, and the primary particles of the cobalt metal contained in the material are present homogeneously distributed in a size of the order of 50 nm to 5 μm, preferably 100 nm to 1 μm.

The grain size of the Co(II) oxide containing cobalt metal according to the invention may be adjusted in accordance with the requirements of different applications by means of various parameters, such as for example concentration, temperature, stirring speed, reaction time, continuous or discontinuous performance of precipitation and various grinding processes before and/or after calcination.

For use in rechargeable alkaline batteries based on Ni/Cd and/or Ni/NiH, average grain sizes of the agglomerates of <3 μm are generally required in order to facilitate homogeneous incorporation into the pastes and to ensure sufficiently rapid dissolution in alkaline electrolytes (30% KOH).

The present invention also provides the use of the Co(II) oxides containing metallic cobalt according to the invention as an electrode material in electrochemical secondary cells.

The invention is illustrated below by way of example, without the invention being limited thereto.

EXAMPLE 1

20 l of water were heated to 85° C. in a stirred reactor. To this were simultaneously added 20 l of a 2 molar aqueous CoCl2 solution and 120 l of an aqueous solution consisting of NaHCO$_3$ (60 g/l) and Na$_2$C2O$_4$ (5 g/l).

The resultant suspension was stirred for 1 h at 85° C., filtered and washed. The resultant product was dried to a constant weight at T=85° C. 4.8 kg of basic cobalt carbonate/oxalate are obtained, which were calcined under an inert gas atmosphere at T=700° C.

The Co content of the resultant product is 80.3%.

EXAMPLE 2

A vessel containing 20 l of water was heated to 85° C. To this were concurrently added 40 l of a 2 molar CoCl2 solution and 60 l of a solution with 150 g/l of Na$_2$CO$_3$ together with 3 g/l of sodium tartrate. Once the reaction was complete, the mixture was stirred for 1 h at T=85° C., suction filtered while hot and washed. The yield obtained was 9.8 kg of basic cobalt carbonate/tartrate, which was subjected to calcination under inert gas at T=700° C.

The Co content of the resultant material amounts to 80.0%.

EXAMPLE 3

170 kg of NaHCO, and 9 kg of tartaric acid were initially introduced into 1 m$^3$ of molar CoCl$_2$ solution at room temperature. The reaction mixture was stirred for 1 h at room temperature, filtered and washed with 500 l of cold water. The filter cake was then suspended in 500 l of water and heated to 85° C. for 2 h, filtered and rewashed while hot. The dried filter cake (120 kg) was subjected to calcination at 7001° C. under protective gas in a rotary kiln. 72 kg of product with a cobalt content of 79.9% were obtained.

What is claimed is:

1. A process for the production of cobalt(II) oxide containing finely divided cobalt metal, wherein aqueous solutions of cobalt salts of the general formula CoX$_2$, wherein X=Cl—, NO$^{3-}$, ½SO4$^2$ are reacted with alkali metal and/or alkaline earth metal and/or ammonium carbonate and/or hydrogen carbonate and/or hydroxide and an organic compound containing at least one carboxyl group, wherein a coprecipitate of the general formula

with $1 \leq a+b+c+d \leq 1.5$, wherein R denotes two identical or different carboxylic acid residues, the molar ratio of which d/(a+b+c+d) is adjusted in accordance with the reductive capacity of the organic residue and the desired cobalt metal content, and, once separated from the solution, the coprecipitate is calcined.

2. The process according to claim 1, wherein one or more carboxylic acids are used as the organic compound containing at least one carboxyll group and/or their salts.

3. The process according to claim 2, wherein the carboxylic acids used are linear or branched saturated or unsaturated monocarboxylic acids with a number of C atoms from 1–9 and/or linear or branched, saturated or unsaturated polycarboxylic acids with a number of C atoms from 2–10 and/or cyclic or heterocyclic, saturated or unsaturated mono- and polycarboxylic acids with a number of C atoms from 4–14 and/or linear or branched, saturated or unsaturated mono- and/or polyhydroxycarboxylic acids with a number of C atoms from 2–7 and/or aromatic hydroxycarboxylic acids with a number of C atoms from 7–11 and/or cyclic or aliphatic, saturated or unsaturated ketocarboxylic acids with a number of C atoms from 2–14.

4. The process according to one of claims 2 or 3, wherein the carboxylic acids used are preferably adipic acid, succinic acid, glutanic acid, glyoxylic acid, maleic acid, malonic acid, lactic acid, oxalic acid, phthalic acids, mucic acid, sorbic acid, racemic tartaric acid, versatic acid, tartaric acid and/or citric acid.

5. The process according to any of claims 1, 2 or 3, wherein partially esterified carboxylic acids are used as the organic compound containing at least one carboxyl group.

6. The process according to any of claims 1, 2 or 3, wherein salts of the carboxylic acids are used as the compound containing at least one carboxyl group.

7. The process according to claim 6 wherein the reaction is performed within a temperature range from 20° C. to 100° C.

8. The process according to claim 7, wherein calcination is performed in an inert gas atmosphere at temperatures of between 200° C. and 1,100° C., preferably 600° C. to 1,000° C.

9. Co(II) oxide containing finely divided metallic cobalt made according to the process of claim 1, wherein it has a cobalt content of between about 78 and 98%, and the primary particles of the cobalt metal contained in the material are present homogeneously distributed in a size of about 50 nm to 5 $\mu$m.

10. An electrode material of a secondary battery comprising the Co(II) oxide containing finely divided metallic cobalt according to one of the claims 1 to 9.

* * * * *